United States Patent [19]

Powell et al.

[11] Patent Number: 5,283,182

[45] Date of Patent: Feb. 1, 1994

[54] PREPARATION OF IMMOBILIZED HYDANTOINASE STABILIZED WITH DIVALENT METAL IONS

[75] Inventors: Lawson W. Powell, Worthing; John A. Power, Faversham, both of England

[73] Assignee: Beecham Group PLC, England

[21] Appl. No.: 486,073

[22] Filed: Feb. 28, 1990

Related U.S. Application Data

[63] Continuation of Ser. No. 98,329, Sep. 17, 1987, abandoned.

[30] Foreign Application Priority Data

Sep. 17, 1986 [GB] United Kingdom ............... 8622389
Sep. 27, 1986 [GB] United Kingdom ............... 8623306

[51] Int. Cl.$^5$ ............... C12P 13/04; C12N 11/08; C12N 11/04; C12N 9/96
[52] U.S. Cl. ............... 435/106; 435/176; 435/178; 435/180; 435/182; 435/188; 435/833
[58] Field of Search ............... 435/106, 176, 178, 180, 435/181, 182, 188, 833

[56] References Cited

U.S. PATENT DOCUMENTS 3,705,084 12/1972 Reynolds ............... 435/180
4,248,967 2/1981 Viglia et al. ............... 435/833 X

FOREIGN PATENT DOCUMENTS 34990 3/1978 Japan ............... 435/106
55-788 5/1979 Japan ............... 435/106
187196 11/1983 Japan ............... 435/106
2042531 9/1980 United Kingdom ............... 435/106
2122621 1/1984 United Kingdom .

*Primary Examiner*—David M. Naff
*Attorney, Agent, or Firm*—Rosenman & Colin

[57] ABSTRACT

An immobilised hydantoinase containing a divalent metal ion selected from $Mn^{++}$, $Co^{++}$, $Fe^{++}$, $Ni^{++}$ and $Mg^{++}$ is produced that is useful for the preparation of a D(−)(optionally substituted phenyl)glycine or N-carbamoyl derivative thereof by hydrolysis of a 5-(optionally substituted phenyl)hydantoin in the absence of air. Immobilization is carried out in the presence of the metal iona nd the metal ion stabilizes the hydantoinase and renders it capable of repeated re-use. The divalent metal ion may also be added to a reaction mixture containing the immobilized hydantoinase to minimize reduction of hydantoinase activity during hydrolysis of hydantoin. Cells that produce hydantoinase may be immobilized within or on a support, or hydantoinase separated from cells can be adsorbed on a positively charged polymeric support such as an ion exchange resin or covalently bonded to a polymeric support. A cross-linking agent such as glutaraldehyde may be used in immobilization. A preferred hydantoinase producing microorganism is *Bacillus brevis* IFO 12333.

8 Claims, No Drawings

PREPARATION OF IMMOBILIZED HYDANTOINASE STABILIZED WITH DIVALENT METAL IONS

This application is a continuation of application Ser. No. 07/098,329, filed Sep. 17, 1987, now abandoned.

This invention relates to an immobilized preparation for use in the production of D(−)α-amino acids by an enzymatic route, and is particularly concerned with a preparation for use in a process for the production of D(−) (substituted phenyl)glycines, such as D(−)(p-hydroxy-phenyl)glycine which is used as a starting material for the production of the antibiotic amoxycillin.

It is known, for example from UK Patent 1452591 and 1506067 that many enzymes exist which are capable of converting 5-(substituted phenyl)hydantoins to D-α-amino acids. The most suitable enzymes are produced by bacterial organisms and UK Patent 1534426 and 1564982 disclose hydantoinase-producing organisms which will hydrolyze 5-(substituted phenyl)hydantoins to D(−)N-carbamoyl-(substituted phenyl)glycines. Moreover UK Patent 1587116 discloses an enzymatic process for producing D-α-amino acid from 5-(substituted phenyl)hydantoin.

It is well known in the art that the immobilization of an enzyme-producing cell, or of the enzyme, leads to a cleaner enzymation liquor, and that this is advantageous for subsequent extraction processes. U.K. Patent 1564982 discloses that cells or treated cells of hydantoinase-producing organisms may be immobilised by conventional techniques. In practice however the immobilized systems thus produced are insufficiently stable to provide a commercially viable process. A commercially viable system must be capable of reuse for a sufficient number of enzymations to recover the cost of its preparation. Typically this would be around 15 times.

Surprisingly it has been found that the presence of a divalent metal ion in such an immobilized enzyme system imparts stability to the preparation so that it is capable of reuse.

Accordingly the present invention provides an immobilized enzyme preparation for use in the production of a D(−)(optionally substituted phenyl)glycine or N-carbamoyl derivative thereof from 5-(optionally substituted phenyl)hydantoin comprising cells or treated cells of an organism which produces a hydantoinase enzyme capable of hydrolyzing 5-(optionally substituted phenyl)hydantoin immobilized within or on a suitable support, or an enzyme derived from the organism adsorbed on a positively charged polymeric support, or covalently bonded to a functionalized polymeric support, together with an effective amount of a stabilizing divalent metal ion.

The effective amount of stabilizing divalent metal ion as described herein will depend upon the ion used and may range from a trace amount, i.e. that which remains bound to the enzyme preparation after an excess of added divalent metal ion has been removed, to a level of, for example, 2 mmolar when the enzyme preparation is suspended in an aqueous medium.

Stabilizing divalent metal ions include divalent ions of metals in Group II of the Periodic Table with the exclusion of zinc, and of certain transition metals which can be divalent. Suitable divalent metal ions may include, for example, $Mn^{++}$ $Co^{++}$, $Fe^{++}$, $Ni^{++}$ and $Mg^{++}$.

Preferred stabilizing divalent metal ions are those of transition metals, in particular $Mn^{++}$, $Co^{++}$ and $Ni^{++}$.

A particularly preferred divalent metal ion is $Mn^{++}$.

By the term D(−)(optionally substituted phenyl)glycine as used herein is meant D(−)phenylglycine and D(−) (mono-, di- or tri-substituted phenyl)glycines. Suitable substituents include hydroxy, $C_{(1-6)}$alkyl, $C_{(1-6)}$ alkoxy and halogen. Preferred D(−)(substituted phenyl) glycines include D(−)(p-hydroxyphenyl)glycine and D(−)(3,4-dihydroxyphenyl)glycine.

The term 5-(optionally substituted phenyl)hydantoin as used herein means 5-phenylhydantoin or 5-(substituted phenyl)hydantoin in which the phenyl is substituted by to three groups including hydroxy, $C_{(1-6)}$alkyl, $C_{(1-6)}$ alkoxy and halogen. Typical examples are 5-(4-hydroxyphenyl)hydantoin and 5-(3,4-dihydroxyphenyl)hydantoin.

The term "immobilized enzyme preparation" as used herein includes immobilized preparations of whole cells, disrupted cells or cell-free enzyme. The enzyme may be crude, partially purified, or purified. Preferably the immobilized enzyme preparation is an immobilized cell-free enzyme preparation.

Preferably the organism from which the hydantoinase enzyme is obtained is a microorganism such as a strain of Bacillus, Pseudomonas, etc. known from UK Patents 1564982, 1587116 and 1534426, or another suitable organism such as a Mycoplana species.

Suitable supports for immobilizing cells or treated cells are those conventionally used in the art such as polymeric matrices including polyacrylamide, polyurethane or calcium alginate or porous organic or inorganic materials such as pumice, alumina and metal foils.

Suitable positively charged polymeric supports for immobilizing cell free enzymes include anion exchange resins and polymeric supports such as DEAE cellulose. Suitable functionalised polymeric supports include substituted polymethacrylic acid polymer functionalised with aldehyde, and materials such as high density alumina coated with a polyethylene imine/glutaraldehyde complex.

Suitable anion exchange resins include strong or weak anion exchange resins, although the latter are preferred. Preferred anion exchange resins include the phenol-formaldehyde anion exchange resins Duolite A568 or Duolite DS 17183 (obtained from Rohm and Haas Company), which are functionalised with secondary amines, polystyrene resins functionalized by tertiary amines such as Amberlite IRA 935, and Amberlite IRA 945 (obtained from Rohm and Haas Company), and Purolit A100. Other suitable resins include Amberlite IRA 901 which is polystyrene functionalized by quaternary ammonium ions and Lewatit OC 1037 (obtained from Bayer AG) which is polystyrene functionalised by primary amines. Polystyrene resins with functional groups of the di-ethanol type, such as Diaion EX-05 (from Mitsubishi Chemical Industries), may also be used.

Stability may be enhanced further by cross-linking the preparation in situ, for example with a water-soluble dialdehyde. A preferred cross-linking agent is glutaraldehyde. In the case of immobilized cell-free enzymes the cross-linking agent is advantageously used at a level below about 1%, preferably at about 0.2%.

In accordance with a further aspect of the present invention there is provided a process for the production of a D(−)(optionally substituted phenyl)glycine or N carbamoyl derivative thereof by the hydrolysis of 5-(optionally substituted phenyl) hydantoin by a suitable hydantoinase enzyme in the absence of air characterised in that the enzyme is provided in the form of an immobilized enzyme preparation comprising cells or treated cells of an organism producing the enzyme immobilized within or on a suitable support, or an enzyme derived from the organism adsorbed on a positively charged polymeric support or covalently bonded to a functionalized polymeric support, together with an effective amount of a stabilising divalent metal ion.

It is essential that air is excluded during the hydrolysis process and subsequently whilst the immobilized cell preparation is recovered and reused The ingress of air has been found to lead to enzyme inhibition, probably by oxidative degradation products of the hydantoin. The reaction is preferably operated under a blanket of nitrogen or other inert gas. It is preferred that nitrogen or rare gas is also bubbled through the reaction mixture In a preferred process of the invention further amounts of stabilizing divalent metal ion, at a level of 0.2-2 mmolar, for example, preferably at a level of 0.5-1.0 mmolar may be added to the reaction mixture. This serves to minimize the reduction of enzyme activity during the reaction.

The hydrolysis reaction is preferably carried out at a pH of at least pH 8, and more preferably in the range 8.5 to 9.5. A preferred pH is about 9.0. This is controlled during the course of the reaction for example by the addition of alkali or by the use of an appropriate buffer. The reaction is normally operated at a temperature in the range 30° to 60° C., most preferably 40° to 50° C. for a period of from 6 to 48 hours, typically 12 to 24 hours.

Suitably the immobilized enzyme preparation is contacted with an aqueous slurry of about 5 to 25% w/v of the 5-(optionally substituted phenyl)hydantoin, preferably 10 to 20% w/v, more preferably about 15% w/v, together with 0.2 to 2, preferably about 0.5, mmolar divalent metal ion. The hydrolysis reaction may be carried out in a stirred tank reactor or in a column reactor in the absence of air.

Certain immobilized enzyme preparations of the invention are capable of hydrolyzing the 5-(optionally substituted phenyl)hydantoin directly to the D(−)(optionally substituted phenyl)glycine. Such enzyme preparations may typically be derived from micro-organisms described in GB 1587116, especially those belonging to the genus Pseudomonas.

Normally, however, the immobilized enzyme preparations of the present invention will hydrolyze the 5-(optionally substituted phenyl)hydantoin to an intermediate D(−)N-carbamoyl(optionally substituted phenyl)glycine, which may subsequently be hydrolyzed, if desired, by chemical or enzymatic methods, to yield the corresponding D(−)(optionally substituted phenyl)glycine.

When it is desired to hydrolyze the intermediate D(−)N-carbamoyl(optionally substituted phenyl)glycine by a chemical method, the reaction may conveniently be carried out with nitrous acid as described by T. Ohashi et al. in *Agric. Biol. Chem.*, 1981, 45(4), 831-838.

Suitable enzymatic methods for hydrolyzing D(−)N-carbamoyl (optionally substituted phenyl)glycines to D(−)(optionally substituted phenyl)glycines involve carbamoylases, as described, for example, in UK Patent No. 2022581.

The immobilized enzyme preparations of the present invention may be stored damp prior to use, preferably at low temperatures such as about 4° C. and may be reused. Immobilized enzyme preparations of the invention have been successfully utilized more than fifteen times, and certain preferred immobilized cell-free enzyme preparations have been reused forty or more times.

In accordance with a further aspect of the invention a process for the production of an immobilized enzyme preparation for use in the production of a D(−)(optionally substituted phenyl)glycine or N-carbamoyl derivative thereof comprises immobilizing treated or untreated cells of an organism which produces a hydantoinase capable of hydrolyzing a 5-(optionally substituted phenyl)hydantoin within or on a suitable support or contacting an enzyme derived from said cells with positively charged or functionalized polymeric support in the presence of an effective amount of stabilizing divalent metal ion.

Techniques for immobilization of the treated or untreated cells within, or on, a suitable support in the presence of an effective amount of a stabilizing divalent metal ion are analogous to those conventionally used in the art. Thus the treated cells may be entrapped within suitable supports such as polymeric matrices including polyacrylamide and polyurethane or calcium alginate or may be chemically bonded to suitable supports such as porous organic or inorganic materials including pumice, alumina and metal foils.

In accordance with a further aspect of the invention a process for the production of an immobilized cell-free enzyme preparation for use in the production of a D(−)(optionally substituted phenyl)glycine or N-carbamoyl derivative thereof comprises preparing a hydantoinase enzyme capable of hydrolyzing a 5-(optionally substituted phenyl)hydantoin, contacting a solution of the enzyme with a positively charged or functionalized polymeric support in the presence of an effective amount of a stabilizing divalent metal ion whereby an immobilized enzyme preparation is produced and separating the immobilized enzyme preparation from an aqueous suspension thereof.

Preferably the hydantoinase enzyme is prepared by fermentation of an appropriate microorganism in a suitable fermentation medium. Suitable microorganism and culture mediums are well known to those skilled in the art and examples thereof are disclosed in UK Patent 1564982, 1534426 and 1587116.

One preferred microorganism is *Bacillus brevis* IFO 12333, which may be grown in the culture medium disclosed in UK Patent 1587116 or similar media. Such media may advantageously include an inducer for the enzyme such as hydantoin or DL-5-methyl hydantoin and divalent metal ions including $Mn^{++}$, $Mg^{++}$, $Co^{++}$ and $Fe^{++}$ which reportedly stimulate hydantoinase production. In a preferred process *Bacillus brevis* is grown in a nutrient seed medium for an appropriate period such as hours, and then grown in a fermentation medium containing the inducing agent and suitable divalent metal ions at about 25° C., a pH of 7 to 8 being maintained during the early phase of growth. Fermentation is complete after about 44 hours.

The cells are then harvested for example by centrifugation, and are then broken by sonication or by other techniques known in the art to release the hydantoinase. In order to partially purify the enzyme it is preferred to precipitate the nucleic acids, for example by the addition of manganous sulphate to a concentration of 20mmolar. To precipitate the heat labile proteins the enzyme is heated to a temperature in the range 50° to 65° C. preferably 55° to 60° C., for approximately 30 minutes followed by cooling to 4° C. The enzyme solution may then be centrifuged to remove cell debris and precipitated nucleic acid and proteins. It is preferred that the enzyme solution is not dialysed prior to adsorption in order to retain the divalent metal ion. In this case it is unnessary to add further divalent metal ion for the production of the immobilised enzyme preparation.

In order to prepare the immobilized cell-free enzyme preparation the partially purified enzyme solution is mixed with the polymeric support in the presence of suitable divalent metal ions. The enzyme loading must be optimised for each type of polymeric support and is typically 3 to 7 units per gram of support. The mixture is agitated at about 25° C. until adsorption has taken place, for example about 24 hours.

The polymeric support is preferably prepared for adsorption by washing in saline solution and equilibrating to about pH 8 to 9.

To cross-link the immobilized cell-free enzyme preparation it is desirable to filter the preparation from the adsorption solution and treat with a solution of cross-linking agent at a pH in the range 8 to 9. The cross-linked preparation may then be washed with distilled water and further buffer, preferably containing a suitable divalent metal ion, prior to damp storage in sealed containers preferably at low temperature such as about 4° C.

Some examples will now be described.

EXAMPLE 1

Hydantoinase enzyme was produced by bacterial fermentations in the following manner. 9 l. of fermentation medium containing the following components was prepared and adjusted to pH 7.0.

| Yeast extract | 200 g |
|---|---|
| $KH_2PO_4$ | 10 g |
| $K_2HPO_4$ | 10 g |
| $(NH_4)_2SO_4$ | 50 g |
| $MgSO_4$ | 5 g |
| $FeSO_4$ | 0.1 g |
| $MnSO_4$ | 0.1 g |
| $CaCl_2$ | 0.8 g |
| Antifoam | 15 g |

The medium was placed in a 12 l. fermenter and autoclaved for 60 minutes at 121° C. Solutions of 20% w/v glucose and 2% DL 5-methyl hydantoin were sterilised separately and 500 mls of each added under sterile conditions to the fermenter.

The fermenter was inoculated with 300 mls of a seed culture of *Bacillus brevis* IFO 12333 grown on Tryptone Soya Broth for 44 hour at 25° C. The fermentation was maintained at 25° C. and aerated at 6 l/min. pH was controlled at 7.0 for 24 hour with HCl. Ammonium hydroxide was then used to raise the pH to 7.5. At 28 hour the pH was raised to 8.0 and then allowed to rise freely.

The fermentation was allowed to proceed for 46 hour when the cells were harvested by centrifugation. The cell pellets were resuspended in 1.25 l. of 0.2M Tris/HCl buffer, pH 8.5. The cells were then sonicated to release the hydantoinase into solution.

Partial purification of the enzyme was carried out as follows: nucleic acids were precipitated by the addition of 20 mM $MnSO_4$, the enzyme solution was heat treated at 58° C. for 30 minutes then cooled to 4° C. After storage at 4° C. for 18 hours the preparation was centrifuged to remove cell debris and precipitated nucleic acid and proteins The preparation was assayed to determine hydantoinase activity A suspension of 1% DL-5-(4-hydroxyphenyl)hydantoin in 0.2M Tris/HCl buffer pH 8.5 was agitated at 42° C. until saturation occurred. An aliquot of the enzyme preparation was then added and the formation of D(−)N-carbamoyl(4-hydroxyphenyl)glycine was followed by HPLC. One unit of hydantoinase is defined as the amount of enzyme that will convert 1 mMol of DL-5-(4-hydroxyphenyl) hydantoin to D(−)N-carbamoyl-(4-hydroxyphenyl)glycine in 1 hour.

EXAMPLE 2

Samples of anion exchange resins obtained from commercial sources were washed for 1 hour in 1M NaCl and then equilibrated overnight in 0.2M Tris HCl buffer pH 8.5. The equilibrated resins were recovered by filtration and stored until required The partially purified enzyme prepared as described in Example 1 was used in the immobilization procedure. The enzyme was allowed to adsorb onto the resins by mixing 10 mls of enzyme solution per gram (damp weight) of resin (3.5–7.0 units/gram resin) for 24 hour at 25° C. The enzyme resin complexes were filtered off and treated with 1% glutaraldehyde at pH 8.5. After 1 hour the resin samples were again filtered off and washed three times with distilled water. Finally, the enzyme-resins were washed with 0.2M Tris/HCl buffer pH 8.5 and stored damp in sealed containers at 4° C.

Each enzyme resin complex prepared in this manner was assayed to determine its specific activity as described in Example 1. Table 1 shows the specific activities obtained for a series of commercial ion-exchange resins treated in this way.

TABLE 1

Specific activities obtained for commerically available anion exchange resins

| NO. | RESIN | SUPPORT MATRIX | FUNCTIONAL GROUPS | ENZYME CHALLENGE u/g | SPECIFIC ACTIVITY u/g |
|---|---|---|---|---|---|
| 1 | DUOLITE DS17183 | Phenol-formaldehyde | 2° Amine | 6.5 | 2.6 |
| 2 | DUOLITE A568 | Phenol-formaldehyde | 2° Amine | 6.5 | 2.51 |
| 3 | PUROLIT A100 | Polystyrene | 3° Amine | 5.27 | 1.42 |
| 4 | AMBERLITE IRA935P | Polystyrene | 3° Amine | 5.15 | 1.89 |
| 5 | AMBERLITE IRA945 | Polystyrene | 3° Amine | 5.15 | 2.06 |
| 6 | AMBERLITE IRA901 | Polystyrene | 4° Ammonium | 3.63 | 0.65 |
| 7 | LEWATIT OC1037 | Polystyrene | 1° Amine | 4.4 | 1.31 |

TABLE 1-continued

Specific activities obtained for commerically available anion exchange resins

| NO. | RESIN | SUPPORT MATRIX | FUNCTIONAL GROUPS | ENZYME CHALLENGE u/g | SPECIFIC ACTIVITY u/g |
|---|---|---|---|---|---|
| 8 | DIAION EX-05 | Polystyrene | Di-ethanol type | 6.0 | 3.3 |

The Duolite and Amberlite resins are commercial products of the Rohm and Haas Company, Philadelphia, U.S.A. The words Duolite and Amberlite are registered trade marks.
The Lewatit resin is a commercial product of Bayer AG, German Federal Republic. The word Lewatit is a registered trade mark.
Diaion resin is a product of Mitsubishi Chemical Industries, Japan. The word Diaion is a registered trade mark.

EXAMPLE 3

440 mls of partially purified enzyme solution (activity =0.59 units/ml) as prepared in Example 1 was added to 40 g of Duolite A568 resin. The mixture was agitated gently at 25° C. for 24 hours to allow the hydantoinase to adsorb to the support. The enzyme-resin complex was then separated by filtration and washed three times with distilled water and finally with 0.2M Tris/HCl buffer pH 8.5. The enzyme resin was stored damp in a sealed container at 4° C. The immobilized enzyme was assayed as described in Example 1 and its specific activity was found to be 3.9 u/g.

200 g of DL-5-(4-hydroxyphenyl)hydantoin and 0.23 g MnSO$_4$ were added to 1.8 l of distilled water in a jacketed vessel. Nitrogen gas was bubbled through the mixture. The suspension was agitated, the temperature controlled at 40° C. and the pH adjusted to 8.7 with ammonium hydroxide. When the system had equilbrated 150 units (38.5 g of enzyme-resin complex) of hydantoinase was added. The reaction was allowed to proceed for 24 hour and the pH controlled at 8.7 with ammonium hydroxide throughout. After 24 hours the yield of D(−)N-carbamoyl-(4-hydroxyphenyl)glycine was determined by HPLC to be 97%. The product formed in this process was isolated by conventional means and found to be of high optical purity.

The enzyme resin used in this process was reused 50 times by decanting the D(−)N-carbamoyl(4-hydroxyphenyl) glycine solution at the end of the reaction, taking care to keep the enzyme under a nitrogen blanket, and replacing it with a fresh charge of pre-equilibrated substrate suspension. Throughout these cycles the conversion yields to D(−)N-carbamoyl(4-hydroxyphenyl)glycine were 95% or greater.

EXAMPLE 4

The hydantoinase enzyme was also immobilized on UOP IPS −100, an alumina based support impregnated with a high molecular weight polethyleneimine-glutaraldehyde complex. UOP IPS-100 is a commercial product of UOP Inc, Des Plaines, Ill. 250 mls of partially purified enzyme solution prepared as described in Example 1 (activity=0.23 units/ml), was added to 7.5 g of UOP support. The mixture was agitated gently at 25° C. for 18 hours. The enzyme-support complex thus formed was separated by filtration and was then washed with distilled water followed by 0.2M Tris/HCl buffer, pH 8.5. The immobilized enzyme was assayed using the standard procedure described in Example 1 and was found to have a specific activity of 4.68 units/g. The insolubilised enzyme was stored damp, in a sealed container at 4° C.

EXAMPLE 5

800 liters of hydantoinase-containing cells of *Bacillus brevis* IFO 12333 were grown up using the medium described in Example 1. The inducer, 5-methyl hydantoin, was sterilised in the medium and the metal ions were dissolved in deionised water and added to the medium just prior to sterilisation. Glucose was added as a sterile 40% w/w solution to give a final concentration of 1% w/v. The medium was inoculated with cells grown for 36 hours at 25° C. in 12 shaken flasks each containing 400 ml of Tryptone Soya Broth. The fermentation was run at 25° C. with 1.0 bar pressure and an airflow of 0.3 v.v.m$^{-1}$. The pH was maintained below 7.0 for the first 36 hours whereupon it was raised to 7.5 from 36 hours until harvest at 48 hours.

The final cell yield was 6.0% with a specific activity of 1.8 u/g.

The cells were harvested using a Westphalia desludging centrifuge and the resultant cell slurry (100 l.) was raised to pH 8.5 with ammonia solution prior to homogenisation in an APV Manton-Gaulin (K6) machine. The homogenate was then diluted to 270 l. with softened water followed by the addition of MnSO$_4$.4-H$_2$O to 20 mM, the pH being maintained at 8.5–8.6 with ammonia solution. This was followed by heat treatment at 60° C. for 1 hour. The flocculated homogenate was then cooled to 30° C. and clarified by passage through a desludging centrifuge.

8.2 kg of anion exchange resin Duolite A568 which had been washed with 1M NaCl and adjusted to pH 8.5 over 1 hour with NH$_4$OH was added to 130 liters of clarified enzyme solution with an activity of 189 u/liter. Adsorption of enzyme to the resin was allowed to take place over 20 hours with agitation, the pH being maintained at 8.5 with NH$_4$OH. The resin was then recovered by filtration and added to 100 liters of 0.2% w/v glutaraldehyde solution at pH 8.5. The cross-linking process occurred over 1 hour with agitation. The enzyme-resin was then recovered by filtration and washed with 0.05M Tris/HCl buffer pH 8.5 containing 1 mM MnSO$_4$ over 30 mins. 8.6 kg of enzyme-resin were recovered with a specific activity of 1.7 u/g.

EXAMPLE 6

6.65 kg of enzyme-resin with an activity of 1.1 u/g prepared by method described in Example 5 was used to hydrolyse 9.75 kg of DL-5-(4-hydroxyphenyl)hydantoin in 65 liters of softened water containing 11 g of MnSO$_4$. The hydrolysis reaction was carried out over 23 hours at 40° C. and pH 9.3–9.5 with N$_2$ being bubbled through the mixture to exclude oxygen. At the end of the reaction a 96.4% yield of D(−)N-carbamoyl(4-hydroxyphenyl)glycine was measured.

EXAMPLE 7

The enzyme-resin in Example 6 was used to carry out 12 hydrolyses of 10% DL-5-(4-hydroxyphenyl)hydantoin at an average yield of 96.4% and further 11 reactions with 15% substrate with an average yield of 95.6%.

EXAMPLE 8

Cells of *Bacillus brevis* IFO 12333 grown up using the medium described in Example 1 were harvested from six liters of fermentation broth by centrifugation. The cells were resuspended to 500 ml in 0.1M Tris buffer pH 9.0 and then mixed with 500 ml or 6% w/v Protanal LP/10/60 (Protan, Drammen, Norway). The cell suspension was then pumped through a syringe needle into a bath of 0.1M calcium chloride solution where cells immobilised in calcium alginate were precipitated and recovered as a thread on a spool. The final weight of immobilised cells was 787.4 g.

A portion of the immobilised cells (330g) was used to hydrolyse 100 g of DL-5-(4-hydroxyphenyl)hydantoin in one liter of water containing 0.44 g of $MnSO_4$. The hydrolysis reaction was carried out over 23 hours at 50° C. and pH 9.1 with $N_2$ being bubbled through the mixture to exclude oxygen. The pH was controlled by the addition of 5M NaOH. At the end of the reaction a 40% yield of D(−)N-carbamoyl(4-hydroxyphenyl)glycine was measured.

We claim:

1. A process for the production of a D(−) (unsubstituted or substituted phenyl) glycine or N-carbamoyl derivative thereof, which comprises:
   1) providing a reusable, divalent metal ion-containing, immobilized enzyme preparation comprising a) cells of an organism producing an hydantoinase enzyme capable of hydrolyzing 5-(unsubstituted or substituted phenyl) hydantoin immobilized within or on a support or b) an hydantoinase enzyme capable of hydrolyzing 5-(unsubstituted or substituted phenyl) hydantoin absorbed on a positively charged polymeric support or covalently bonded to functional groups of a polymeric support and c) an amount effective to stabilize said immobilized enzyme preparation so that it is capable of reuse of a stabilizing divalent metal ion selected from the group consisting of $Mn^{++}$, $Co^{++}$, $Fe^{++}$, $Ni^{++}$ and $Mg^{++}$;
   2) hydrolyzing a 5-(unsubstituted or substituted phenyl) hydantoin in the absence of air by said reusable, divalent metal ion-containing, immobilized enzyme preparation to form a reaction product comprising D(−)(unsubstituted or substituted phenyl) glycine or N-carbamoyl derivative thereof;
   3) separating said reusable, divalent metal ion-containing, immobilized enzyme preparation from said reaction product;
   4) hydrolyzing fresh reactant comprising a 5-(unsubstituted or substituted phenyl) hydantoin in the absence of air by said reusable, divalent metal ion-containing, immobilized enzyme preparation recovered from step 3; and
   5) repeating steps 2–4 for a plurality of cycles, whereby said recovered immobilized enzyme preparation is repeatedly reused to produce D(−)(unsubstituted or substituted phenyl) glycine or N-carbamoyl derivative thereof.

2. The process according to claim 1, wherein said divalent, metal ion is $Mn^{++}$, $Co^{++}$ or $Ni^{++}$.

3. The process according to claim 1, in which said divalent metal ion is $Mn^{++}$.

4. The process according to claim 1, in which the reusable, divalent metal ion-containing immobilized enzyme preparation is cell-free.

5. The process according to claim 1, in which said hydantoinase enzyme is obtained from a strain of Bacillus, Pseudomonas or Mycoplana.

6. The process according to claim 1, in which said hydantoinase enzyme is obtained from *Bacillus brevis* IFO 12333.

7. The process according to claim 1, in which said reusable, divalent metal ion-containing, immobilized enzyme preparation is crosslinked.

8. The process according to claim 1, in which D(−)(4-hydroxyphenyl) glycine or D(−)N-carbamoyl(4-hydroxyphenyl) glycine is produced.

* * * * *